(12) United States Patent
Warwick et al.

(10) Patent No.: US 6,958,046 B2
(45) Date of Patent: Oct. 25, 2005

(54) CHEST COMPRESSION APPARATUS

(76) Inventors: Warren J. Warwick, 1952 E. River Ter., Minneapolis, MN (US) 55414; Leland G. Hansen, 2309 Beverly Rd., St. Paul, MN (US) 55104

( * ) Notice: Subject to any disclaimer, the term of this patent is extended or adjusted under 35 U.S.C. 154(b) by 0 days.

(21) Appl. No.: 10/038,208

(22) Filed: Jan. 2, 2002

(65) Prior Publication Data

US 2002/0111571 A1 Aug. 15, 2002

Related U.S. Application Data

(63) Continuation of application No. PCT/US00/18037, filed on Jun. 29, 2000.
(60) Provisional application No. 60/142,112, filed on Jul. 2, 1999.

(51) Int. Cl.[7] .................................................. A61H 9/00
(52) U.S. Cl. ........................ 601/44; 601/148; 601/151; 601/152
(58) Field of Search .............................. 601/41, 43, 44, 601/48, 148, 149, 150, 151, 152; 128/DIG. 20, 205.24

(56) References Cited

U.S. PATENT DOCUMENTS

| | | | |
|---|---|---|---|
| 2,354,397 A | 7/1944 | Miller | |
| 2,588,192 A | 3/1952 | Akerman et al. | |
| 3,043,292 A | 7/1962 | Mendelson | |
| 3,307,533 A | 3/1967 | Meredith et al. | |
| 3,310,050 A | 3/1967 | Goldfarb | |
| 3,462,778 A | * 8/1969 | Whitney | 601/150 |
| 4,135,500 A | * 1/1979 | Gorran | 601/150 |
| 4,197,837 A | * 4/1980 | Tringali et al. | 601/150 |
| 4,311,135 A | * 1/1982 | Brueckner et al. | 601/152 |
| 4,838,263 A | 6/1989 | Warwick et al. | 128/30.2 |
| 4,977,889 A | 12/1990 | Budd | 128/30.2 |
| 5,056,505 A | * 10/1991 | Warwick et al. | 601/44 |
| 5,453,081 A | * 9/1995 | Hansen | 601/150 |
| 5,569,170 A | 10/1996 | Hansen | 601/150 |
| 5,769,797 A | 6/1998 | Van Brunt et al. | 601/41 |
| 6,030,353 A | * 2/2000 | Van Brunt | 601/150 |
| 6,182,658 B1 | * 2/2001 | Hayek | 128/205.24 |

FOREIGN PATENT DOCUMENTS

| | | |
|---|---|---|
| WO | WO 95/32753 | 12/1995 |
| WO | WO 98/49993 | 11/1998 |

* cited by examiner

*Primary Examiner*—Nicholas D. Lucchesi
*Assistant Examiner*—Quang D. Thanh
(74) *Attorney, Agent, or Firm*—Fredrikson & Byron, P.A.

(57) ABSTRACT

A chest compression apparatus for use by patients with cystic fibrosis, the preferred apparatus including an air flow generator component, a pulse frequency control component having a fan blade valve for producing a sinusoidal wave form, an optional pressure control component, and a patient vest. The apparatus can be used to apply sharp compression pulses to the entire thorax via the inflatable vest worn by the patient. The optional modular nature of the present apparatus provides particular benefits in the manufacture and use of the present apparatus. The modular nature, in essence, provides even greater portability since one or more modules can be individually replaced or repaired as needed, thereby lessening the overall cost and inconvenience to the patient.

40 Claims, 4 Drawing Sheets

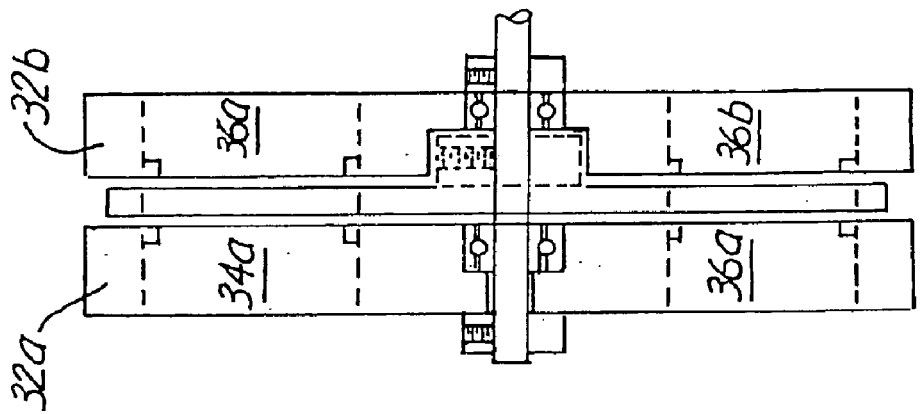
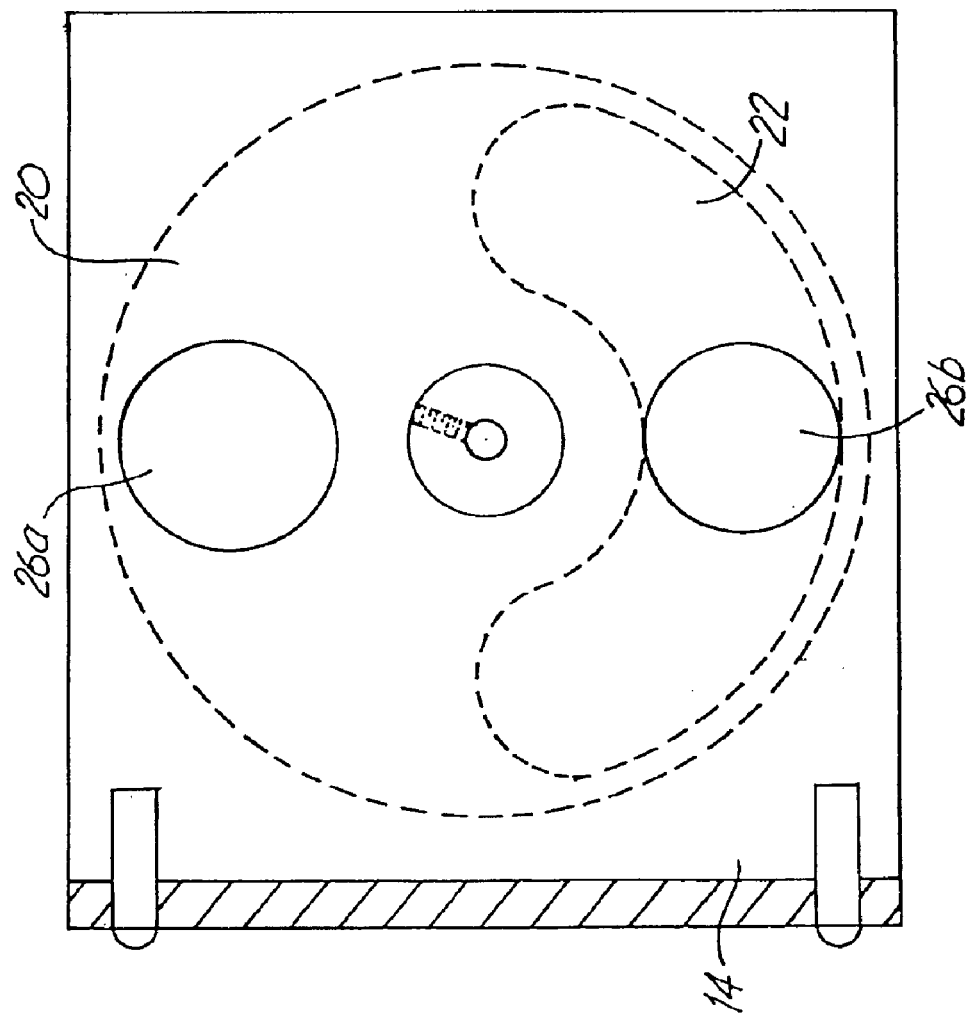
FIG. 2

CHEST COMPRESSION APPARATUS

CROSS REFERENCE TO RELATED APPLICATIONS

The present application is a continuation of and claims priority to International Application No. PCT/US00/18037 (published as International Publication No. WO 01/01918), filed 29 Jun. 2000 and designating the United States, which in turn claims priority from provisional application having U.S. Ser. No. 60/142,112, filed 2 Jul. 1999, the entire disclosure of which is incorporated herein by reference.

TECHNICAL FIELD

The present invention relates to oscillatory chest compression apparatuses, and in particular, those used for clearing mucous from the lungs, as in patients with cystic fibrosis.

BACKGROUND OF THE INVENTION

Cystic fibrosis is a deadly hereditary disease. With one in 20 people carrying the recessive gene, conception of a child having cystic fibrosis results in approximately one in every 400 child-bearing marriages. No cure for the disease has yet been discovered. Cystic fibrosis affects the mucus secreting glands of the body, leading to an overproduction of mucus. The lungs are continuously filled with the excess mucus, which in turn must be removed daily to reduce the build-up and the risk of infection. Presently, treatment generally involves an aerosol therapy three or four times a day to obtain bronchial drainage and a daily physical pounding on the chest wall to loosen mucus for expectoration. Daily treatment can range from four to six hours plus and necessitates a respirator therapist or at least a trained individual to provide the pummeling of the chest.

The art in the area of mechanical vibrations to the body shows such things as inflatable jackets or garments to put on a person to aid in respiration, such as artificial respiration. U.S. Pat. Nos. 3,043,292, 2,354,397, 2,588,192 are representative. Additionally, a garment which provides oscillations for the purpose of massaging the body is shown in U.S. Pat. No. 3,310,050.

In more recent years, a variety of high frequency chest compression ("HFCC") systems have been developed to aid in the clearance of mucus from the lung. Such systems typically involve the use of an air delivery device, in combination with a vest to be worn by a patient, with the two being connected by a valve or other device that permits the pulsed flow of air to the vest. Such vests were developed for patients with cystic fibrosis, and are designed to provide airway clearance therapy. The patient wears an inflatable vest that is linked to an air pulse generator that rapidly inflates and deflates the vest during inspiration and/or expiration. The compression pulses produce transient cephalad air flow bias spikes in the airways, which moves mucous toward the larger airways where it can be cleared by coughing. The prior vest systems differ from each other, in at least one respect, by the valves they employ (if any), and in turn, by such features as their overall weight and the wave form of the air produced.

Related patents describe systems having a variety of attributes, e.g., those in which an air stream is interrupted, as by the use of a regenerative blower with a rotary interrupt valve. Such systems are typified by a "quick dump", high volume rotary valve (also known as a "tube valve" or "chopper valve"). These types of valves typically produced a pulse form that most closely approximated near square wave pulses at about 10 to 20 Hz (i.e., not true sine waves), but which are said to become more sinusoidal as the frequency is decreased to 5 Hz.

U.S. Pat. No. 4,838,263 (Warwick et al.) describes an apparatus in which the application of pressurized pulses and the pulse rate are each controllable by the patient. The device addresses the desire of some patients to have the device provide less of a "thump" during inhalation. The device, in turn, permits the user to controllably cut the thumping pressure. In operation, the tank delivers air into the bladder, and the patient uses either a pedal to deliver more air and/or a thumb positioned over a tube, in order to release pressure.

U.S. Pat. No. 5,056,505 for a "Chest compression apparatus", invented by Warwick and Hansen relates to an oscillatory chest compression apparatus to aid in loosening and eliminating mucus from the lungs of a cystic fibrosis patient. The '505 patent describes an apparatus, including a valve that can be used to deliver a sharply spiked air pulse, such that the slope (rise time) of the pulse is defined as being at least twice as fast as that of a sinusoidal wave of the same frequency and amplitude. The valve itself involves the use of leading and following edges that serve to abruptly start and stop the flow of air. During inspiration, the atmospheric phase, the positive pressure side of the system can be blocked. The pressure pulse wave form is a function of the shape and size of the rotary valve ports and the pressure applied to the valve. The quick dump design of the valve ports allows for maximum opening in a short time. A constant pressure air stream is chopped into pulses and directed to the inflated vest.

Hansen U.S. Pat. No. 5,569,170 (assigned to Electromed, Inc. Minnetonka, Minn.) is directed to yet another alternative in which a speaker-like diaphragm is employed to deliver the pulses in the form of repetitive pressure pulses, much along the lines of a pulsating speaker.

U.S. Pat. No. 4,977,889 (Budd), in turn, describes an algorithm for use in tuning such an apparatus to a particular patient. The algorithm can be used to improve the effectiveness (mucous generation and air flow spikes) of any chest compression apparatus. Presently, doctors having such software can use the algorithm to set any particular device for a particular patient.

Finally, Van Brunt et al. (U.S. Pat. No. 5,769,797, "Oscillatory chest compression device") describes a compression device that includes an oscillatory air flow generator and a positive air flow generator. A first feedback system controls the oscillation rate of the oscillatory air flow generator, and a second feedback system controls the peak pressure created by the positive air flow generator.

Certain of the approaches described above have been embodied in various prototypes and/or commercial devices that have been previously developed. Applicant's own initial "Model 101", and later "Model 102" were developed and used previously, both employing a rotary ("chopper") valve, of the type described in the above-captioned '505 patent. These devices provided wave forms having a near square wave pulse form.

Currently, American Biosystems, Inc. markets a device ("Model 103") under the tradename "ThAIRapy Vest", as a device designed for self-administration of chest physical therapy for patients with cystic fibrosis and other chronic lung disorders. The vest is said to be a portable device that uses a technology called high frequency chest wall oscillation to provide airway clearance therapy. The vest includes an inflatable vest linked to an air pulse generator that inflates and deflates the vest from 5 to 25 times per second. This creates a high expiratory flow within the lungs which moves mucous toward the larger airways where it can be cleared by coughing. The device appears to include the use of a diaphragm driven by an electromagnet, which appears to provide a sine wave pulse form.

The units presently in commercial use, however, continue to be quite expensive, as well as large and heavy, and hence are not considered particularly portable. The community of patients suffering from these disease therefore continues to seek affordable devices that can provide comparable or improved features and performance, in a manner that provides improved portability.

BRIEF DESCRIPTION OF THE DRAWING

In the Drawing:

FIG. 2 shows a prototypical fan valve for use in an apparatus of this invention.

SUMMARY OF THE INVENTION

Figure 1:
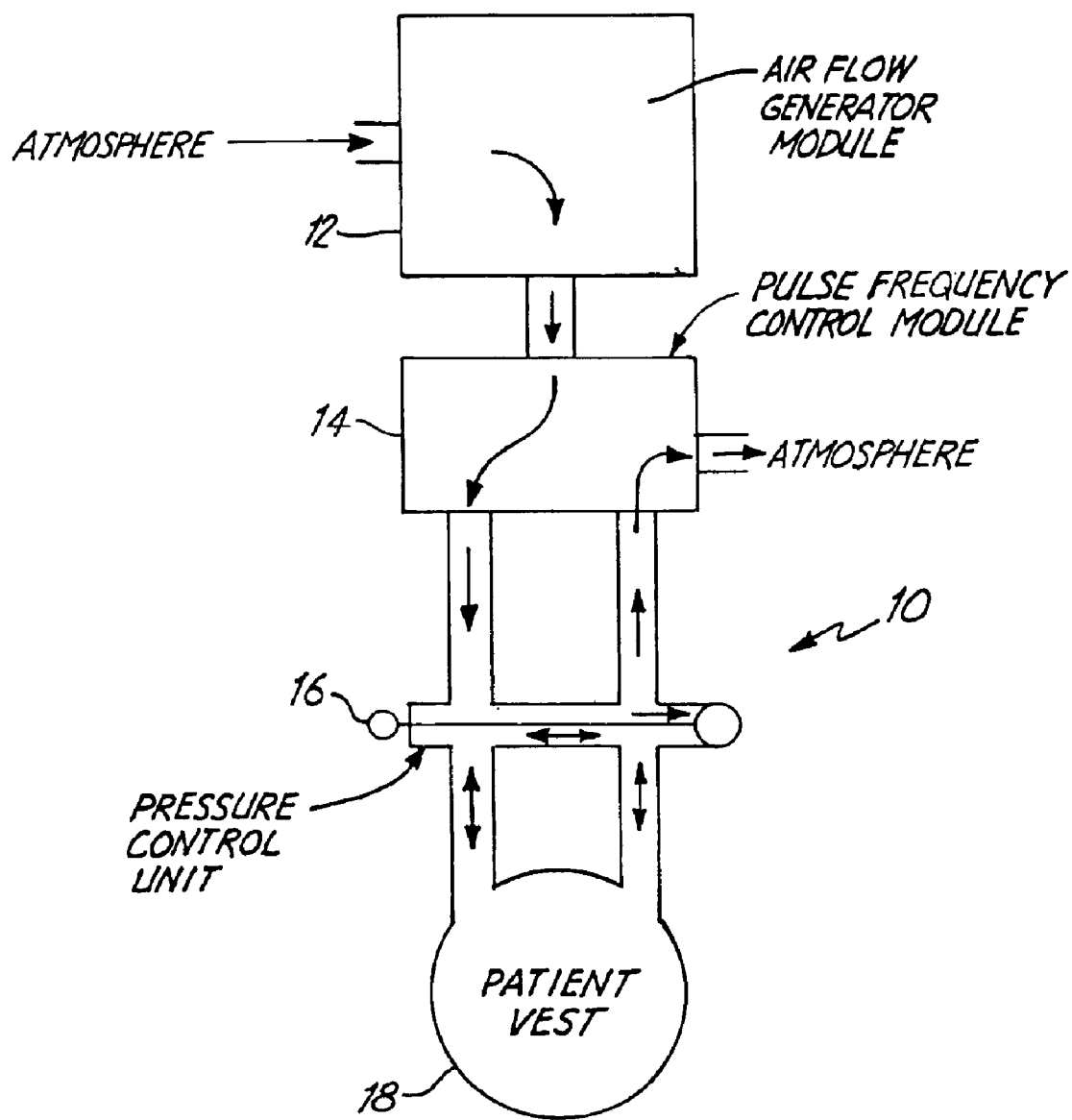
FIG. 1 shows a schematic air flow diagram for an apparatus of this invention.

The present invention is directed to a chest compression apparatus for the thoracic region of a person. The apparatus includes a mechanism for applying a force to the thoracic region of the person. The force applying mechanism includes a bladder for receiving pressurized air. The apparatus further includes a mechanism for supplying pressure pulses of pressurized air to the bladder, the pulses having a sinusoidal wave form. The present apparatus, and in turn, the pulse form it delivers, provide several advantages over previous apparatuses, e.g., those of the '505 patent described above (in which a rotary valve is used to provide a pulse form said to have a rise time at least twice as fast as the rise time of a sinusoidal pulse of equivalent amplitude frequency). Additionally, the apparatus optionally includes a mechanism for venting the pressurized air from the bladder. In addition to performance that is comparable to, if not better than, that provided by prior devices, the apparatus of the present invention can be manufactured and sold for considerably less than current devices, and can be provided in a form that is far more modular and portable than existing devices.

In a preferred embodiment, the apparatus comprises a plurality of components, including an air flow generator component, a pulse frequency control component, a pressure control component, and a patient vest, wherein the pulse frequency control and pressure control components can, independently, be used by the patient and/or can be preset and determined by the manufacturer or physician so as to deliver compression pulses having substantially sinusoidal wave forms.

In a particularly preferred embodiment, the invention provides a chest compression apparatus comprising:

a) an air flow generator component adapted to provide a continuous stream of pressurized air, b) a pulse frequency control component in flowable communication with the air flow generator and comprising a fan valve adapted to periodically interrupt the air stream in order to provide pulses having a substantially sinusoidal wave form, c) optionally, a pressure control component in flowable communication with the pulse frequency control component and adapted to permit a user to control the pressure of the pulses, and d) a patient vest adapted to be worn by a user in order to receive the pulses in the form of corresponding force applied to the thoracic region.

The components of such an apparatus can be provided in the form of a plurality of portable modules having a combined weight of about 20 pounds or less, preferably about 15 pounds or less, and the apparatus provides a maximum pressure of about 60 mm Hg or less.

An apparatus of this invention can be used to apply sharp compression pulses to the entire thorax via an inflatable vest worn by the patient. The compression pulses produce transient cephalad airflow bias spikes in the airways. The airflows in the lungs are similar to those occurring in a huffing maneuver with its associated mucous shear flow. These higher airflow spikes produce the more desirable shear forces necessary for effective mucous clearance.

In a preferred embodiment of the present invention, a fan valve is used to establish and determine the rate and duration of air pulses entering the bladder from the pressure side and allows air to evacuate the bladder on the depressurizing side. An air generator (e.g., blower) is used on the pressurizing side of the fan valve. The fan valve advantageously provides a substantially sinusoidal pulse, which can be provided through a port opened to provide communication between the blower and the bladder. Although not necessary, the preferred embodiment also includes a pressure control unit including a control switch. The control switch can function a solenoid valve on the pressurizing side of the fan valve to decrease or stop pressurization during the inspiration portion of the patient's breathing cycle, depending on the desire of the patient.

The present apparatus provides a variety of solutions and options to the treatment problem faced by people having cystic fibrosis. The advantages of the invention relate to benefits derived from a treatment program using the present apparatus rather than a conventional device having a rotary valve and corresponding pulses. In this regard, a treatment program with the present apparatus provides a cystic fibrosis patient with independence in that the person can manipulate, move, and operate the machine alone. He/she is no longer required to schedule treatment with a trained individual. This results in increased psychological and physical freedom and self esteem. The person becomes flexible in his/her treatment and can add extra treatments, if desired, for instance in order to fight a common cold. An additional benefit is the corresponding decrease in cost of treatment, as well as a significant lessening of the weight (and in turn, increased portability) of the device itself.

The optional modular nature of the present apparatus provides particular benefits in the manufacture and use of the present apparatus. The modular nature, in essence, provides even greater portability since one or more modules can be individually replaced or repaired as needed, thereby lessening the overall cost and inconvenience to the patient. Moreover, the patient can keep duplicate or different versions of one or more modules at different locations, e.g., at work and at home, meaning that he or she need only transport the remaining modules in order to use the apparatus.

DETAILED DESCRIPTION

With reference to the Drawing, FIG. 1 shows a prototypical air flow diagram associated with an apparatus 10 of this invention. The apparatus includes an air flow generator component 12, flowably connected to a pulse frequency control module 14, which in turn is flowably connected to a pressure control unit 16, and finally to a vest 18 worn by the patient. In use, the air flow generator (e.g., motor driven blower) delivers pressurized air to the vest, via a pulse frequency control unit that preferably includes one or more rotating (e.g., fan-like) blades.

Such a blade is shown in FIG. 2, wherein the unit 14 is shown in cross section and on end. The prototype shown includes a generally circular valve blade assembly 20, rotatable upon a central axis and having one or more cutout portions 22. The blades are retained on a centrally located motor driven shaft 24, which serves to rotate the blades, and in turn, provide airflow access to and through the cutout portion(s) in front the end plates of air ports 26*a* and 26*b*, respectively. Optionally, and as shown, the blades are connected to the drive shaft by means of a blade support collar 28 and set screw 30.

In a prototypical embodiment, the air flow generator is provided in the form of a compact air pulse delivery apparatus that is considerably smaller than those presently or previously on the market (e.g., on the order of one-fifth to one-tenth the size and weight of the original Model 101), with no single modular component of the present apparatus weighing more than about 10 pounds. Hence the total weight of the present apparatus can be on the order of 20 pounds or less, and preferably on the order of 15 pound or less, making it considerably lighter and more portable than devices presently on the market. In an initial prototype, the air flow generator module is provided in the form of a conventional motor and fan assembly, and is enclosed in a compartment having air inlet and outlet ports. The air inlet port can be open to atmosphere, while the outlet port can be flowably coupled to the pulse frequency module.

In spite of its compact and optionally modular nature and relatively low weight, the apparatus of the present invention can provide pressurized pulses of on the order of 60 mm Hg or less, as compared to the current version of the aforementioned Model 103, which appears to limited to pulses of on the order of 40 mm Hg or less. The ability to provide pulses having higher pressure, while also minimizing the overall size and weight of the unit, is a particular advantage of the present apparatus as well. Pulses of over about 60 mm Hg are generally not desirable, since they can tend to lead to bruising.

As shown in FIG. 2, a pair of end plates 32*a* and 32*b* are mounted on an axis concentric with that of motor drive shaft, and effectively sandwich the blade assembly between them. The end plates are provided with corresponding air ports 34*a* and 36*a* (in plate 32*a*) and 34*b* and 36*b* (in plate 32*b*). The air ports are overlapping such that air delivered from the external surface of either end plate will be free to exit the corresponding air port in the opposite plate, at such times as the blade cutout portion of the valve blade is itself in an overlapping position therebetween. By virtue of the rotation of cutout portions past the overlapping air ports, in the course of constant air delivery from one air port toward the other, the rotating fan blade effectively functions as a valve to permit air to pass into the corresponding air port in a semi-continuous and controllable fashion. The resultant delivery tends to take a sinusoidal wave form, by virtue of the shape and arrangement of the fan blade Cutout portions.

Figure 3:
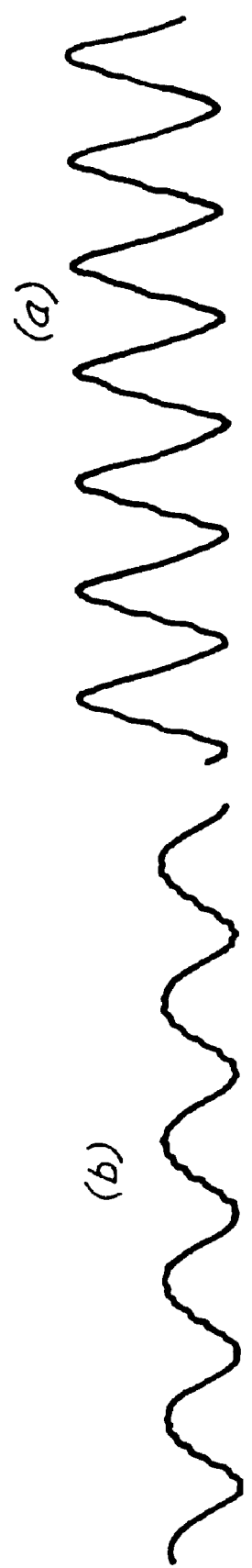
FIG. 3 shows a comparative plot of a wave form (a) provided by a rotating blade of this invention as compared to a wave form (b) provided by a reciprocating diaphragm of the type described above.

The pulse frequency module, in a preferred embodiment, is provided in the form of a motor-driven rotating blade ("fan valve") adapted to periodically interrupt the air stream from the air flow module (FIG. 2). During these brief interruptions air pressure builds up behind the blade. When released, as by the passage of the blade, the air travels as a pressure pulse to the vest worn by the patient. The resulting pulses are in the form of fast rise, sine wave pressure pulses. These pulses, in turn, can produce significantly faster air movement in the lungs, in the therapeutic frequency range of about 6 Hz to about 15 Hz, as measured at the mouth. These can be compared to the sinusoidal wave pulses such as those produced by the reciprocating diaphragm (FIG. 3). In combination with higher flow rates into the lungs, as achieved using the present apparatus, these factors result in stronger mucus shear action, and thus more effective therapy in a shorter period of time.

Those skilled in the art will understand the manner in which a fan valve of the present invention can be adapted (e.g., by configuring the dimensions, pitch, etc. of one or more fan blades) to provide wave pulses in a variety of forms, including sine waves, near sine waves (e.g., waves having precipitous rising and/or falling portions, as provided by the rotary valve of the above-described '505 patent), and complex waves. As used herein a sine wave can be generally defined as any uniform wave that is generated by a single frequency, and in particular, a wave whose amplitude is the sine of a linear function of time when plotted on a graph that plots amplitude against time. The pulses can also include one or more relatively minor perturbations or fluctuations within and/or between individual waves, such that the overall wave form is substantially as described above. Such perturbations can be desirable, for instance, in order to provide more efficacious mucus production in a manner similar to traditional hand delivered chest massages. Moreover, the pulse frequency module of the present invention can be programmed and controlled electronically to allow for the automatic timed cycling of frequencies, with the option of manual override at any frequency.

Figure 4:
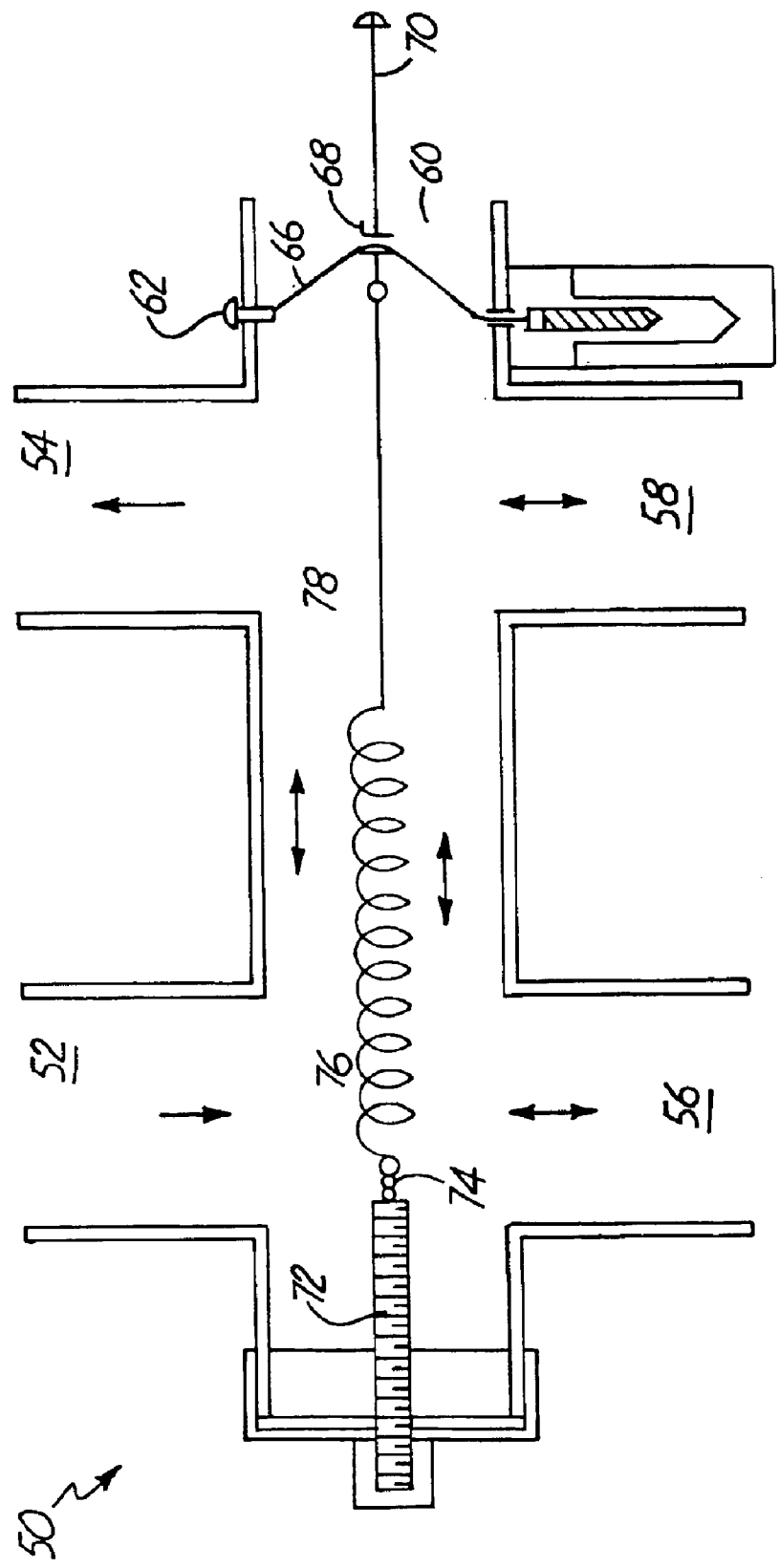
FIG. 4 shows a diagramatic representation of a suitable pressure control unit for use in an apparatus of the present invention.

As a further component, the apparatus includes a pressure control unit, e.g., having features and functions of the prototype 50 depicted in FIG. 4. The component includes an air inlet port 52 adapted to receive air from the exit port of the pulse frequency control module, and effectively provides a manifold to controllably deliver that air to the vest or atmosphere by means of any suitable combination of vest exit ports 54, 56, and 58, and to the atmosphere by means of exit port 60. Finally, a pulse pressure control can be located between the frequency control module and the vest worn by the patient (FIG. 4).

Lightweight flexible tubing connects the vest, pressure control and pulse frequency module. In a preferred embodiment, the pressure control unit consists of a five port manifold, in which two are attached to the vest itself, and two are connected to the pulse frequency control module. The fifth is the pulse pressure port, which is covered by a floating rubber sphere which is held in place over the port by a spring tether having adjustable tension. Adjusting the tension on the spring provides a means of controlling the amplitude of the pulses while still maintaining a sharp pulse form. The tension can also be controlled electronically to allow bilevel pulse pressure (FIG. 4). In this mode, a breath sensing device can be used to signal the pressure control unit to shift to a lower pulse pressure amplitude on inspiration and return to a higher amplitude during expiration. Yet, the sharp pulse wave form can be maintained regardless of pressure range, with manual override again being an option at any point throughout the cycle.

During patient respiratory inspiration the apparatus pulse pressure can be reduced by opening to atmosphere ball 70.

This can be accomplished either manually or electronically. During patient exhalation ball valve 70 is in the closed position for maximum peak pulse pressure, or allowed to operate as a maximum pressure relief valve controlled by adjusting spring 76. The manifold receives HFCC pulse pressure waves through port 52 through the frequency control port 26a. Port 54 is shown connected to port 26b of the frequency control module and is closed to atmosphere when 26a is open and open when 26a is closed. Ports 56 and 58 are connected to the inflatable vest via flexible tubing, with the vest itself being worn by the patient.

HFCC therapy is prescribed as either an adjunct or outright replacement for manual chest physiotherapy. Total therapy time per day varies between about 30 minutes and about 240 minutes spread over one to four treatments per day. Patients can be instructed in either the continuous intermittent mode of HFCC therapy, which may include continuous use of aerosol.

During HFCC therapy the patient sits erect, although leaning against a chair back is acceptable as long as air flow in the vest is not restricted. In the continuous mode, the patient operates the vest for 5 minutes at each of six prescribed frequencies (determined by "tuning" performed during a clinic visit). The patient uses the hand control to stop pulsing as frequently as necessary to cough, usually every several minutes.

In the intermittent mode, the patient uses the hand control to stop pulsing during inspiration to make it easier to inhale maximally. The pulsing is activated again during each expiration. Longer pauses for coughing are taken as needed. The patient goes through the cycle of prescribed frequencies determined by tuning during a clinic visit.

An apparatus of the present invention can be used in the following manner. A vinyl coated polyester inflatable vest is made for each patient, to cover the entire torso from the shoulders to the iliac crest and to fit snugly when the patient inspires to total lung capacity. The optimal design, function and performance of such a vest can be determined by those skilled in the art, based on the present description.

The vest is "tuned" for each individual to determine the volume of air expressed from the lung and the rate of flow of this air for each chest compression frequency (e.g., from about 5 Hz to about 22 Hz). The flow rates and volume are calculated with a computer program from flow data obtained during tidal breathing through a Hans Rudolph pulmonary pneumotachometer with pinched nose. The frequencies associated with the highest flow rates are usually greater than 13 Hz, while those associated with largest volume are usually less than about 10 Hz. These best frequencies vary from patient to patient. Since the highest induced flow rates usually do not correspond with largest induced volumes, and since 2 to 3 were commonly very close in value, the three highest flow rates and the three largest volumes are selected for each patient's therapy. Occasionally one frequency is selected twice because it produces one of the three highest flow rates and one of the three largest volumes. Each of these six frequencies is prescribed for five minutes for a total of 30 minutes each therapy session. Since the best frequencies change over time with the use of the vest, re-tuning should be performed every 3 to 6 months.

One explanation of the way in which HFCC moves mucus is derived from observations of the perturbations of air flow during tidal breathing and during maximum inspiration and exhalation to residual volume. Each chest compression produces a transient flow pulse very similar to the flow observed with spontaneous coughing. Tuning identifies those transient flows with the greatest flows and volumes, in effect the strongest coughs, and analogously with the greatest power to move mucus in the airways.

What is claimed is:

1. A chest compression apparatus comprising
   a) a mechanism for applying a force to the thoracic region of a person, the mechanism comprising a bladder for receiving a stream of pressurized air, and
   b) a mechanism comprising a motor-driven rotating blade adapted to periodically interrupt the stream of pressurized air to the bladder in order to provide pressure pulses having a substantially sinusoidal wave form that comprises a fast rise sine wave when applied at a frequency of 6 Hz.

2. An apparatus according to claim 1 further comprising a mechanism for venting the pressurized air from the bladder.

3. An apparatus according to claim 1 wherein the apparatus comprises a plurality of components, including an air flow generator component, a pulse frequency control component, a pressure control component, and a patient vest wherein the pulse frequency control and pressure control components can, independently, be used by the patient or can be preset and determined by the manufacturer or physician as to deliver compression pulses having substantially sinusoidal wave forms.

4. An apparatus according to claim 3 wherein the pulse frequency control component is programmed and controlled electronically to allow for the automatic timed cycling of frequencies.

5. An apparatus according to claim 4 wherein the pulse frequency control provides the option of manual override at any frequency.

6. A chest compression apparatus according to claim 1, comprising:
   a) an air flow generator component adapted to provide a continuous stream of pressurized air,
   b) a pulse frequency control component in flowable communication with the air flow generator, and
   c) a patient vest adapted to be worn by a user in order to receive the pulses in the form of corresponding force applied to the thoracic region.

7. An apparatus according to claim 6 further comprising a pressure control component in flowable communication with the pulse frequency control component and adapted to permit a user to control the pressure of the pulses.

8. An apparatus according to claim 6 wherein the apparatus is provided in the form of a plurality of portable modules having a combined weight of about 20 pounds or less.

9. An apparatus according to claim 8 wherein the apparatus modules have a combined weight of 15 pounds or less.

10. An apparatus according to claim 1 wherein the apparatus provides a maximum pressure of about 60 mm Hg or less.

11. An apparatus according to claim 1 wherein the rotating blade is used to establish and determine the rate and duration of air pulses entering the bladder.

12. A chest compression apparatus according to claim 1, further comprising
    a mechanism for venting the pressurized air from the bladder,
    wherein the apparatus is provided in the form of a plurality of portable modules having a combined weight of about 20 pounds or less and provides a maximum pressure of about 60 mm Hg or less.

13. An apparatus according to claim 1 further comprising a mechanism for venting the pressurized air from the bladder, wherein the apparatus comprises a plurality of components, including an air flow generator component, a pulse frequency control component, a pressure control component, and a patient vest, wherein the pulse frequency control and pressure control components can, independently, be used by the patient or can be preset and determined by the manufacturer or physician so as to deliver compression pulses having substantially sinusoidal wave forms.

14. A chest compression apparatus according to claim 13, wherein:
   a) the air flow generator component adapted to provide a continuous stream of pressurized air,
   b) the pulse frequency control component is in flowable communication with the air flow generator, and
   c) the patient vest adapted to be worn by a user in order to receive the pulses in the form of corresponding force applied to the thoracic region.

15. An apparatus according to claim 14 wherein the pressure control component is in flowable communication with the pulse frequency control component and adapted to permit a user to control the pressure of the pulses.

16. An apparatus according to claim 15 wherein the apparatus is provided in the form of a plurality of portable modules having a combined weight of 15 pounds or less and the apparatus provides a maximum pressure of about 60 mm Hg or less.

17. An apparatus according to claim 16 wherein the rotating blade is used to establish and determine the rate and duration of air pulses entering the bladder.

18. A method of applying a force to the thoracic region of a person comprising the steps of providing and using an apparatus according to claim 13.

19. A method according to claim 18 wherein the apparatus is provided in the form of a plurality of portable modules having a combined weight of 15 pounds or less and the apparatus provides a maximum pressure of about 60 mm Hg or less.

20. A method according to claim 19 the wherein the rotating blade is used to establish and determine the rate and duration of air pulses entering the bladder.

21. An apparatus according to claim 1 wherein the pulses include one or more minor perturbations or fluctuations within or between individual waves or both.

22. A method of applying a force to the thoracic region of a person comprising the steps of providing and using an apparatus according to claim 1.

23. A method according to claim 22 wherein the apparatus further comprises a mechanism for venting the pressurized air from the bladder.

24. A method according to claim 22 wherein the apparatus comprises a plurality of components, including an air flow generator component, a pulse frequency control component, a pressure control component, and a patient vest, wherein the pulse frequency control and pressure control components can, independently, be used by the patient or can be preset and determined by the manufacturer or physician so as to deliver compression pulses having substantially sinusoidal wave forms.

25. A method according to claim 24 wherein the pulse frequency control component is programmed and controlled electronically to allow for the automatic timed cycling of frequencies.

26. A method according to claim 22 wherein the apparatus comprises
   a) an air flow generator component adapted to provide a continuous stream of pressurized air,
   b) a pulse frequency control component in flowable communication with the air flow generator, and
   c) a patient vest adapted to be worn by a user in order to receive the pulses in the form of corresponding force applied to the thoracic region.

27. A method according to claim 26 further comprising a pressure control component in flowable communication with the pulse frequency control component and adapted to permit a user to control the pressure of the pulses.

28. A method according to claim 26 wherein the apparatus is provided in the form of a plurality of portable modules having a combined weight of about 20 pounds or less.

29. A method according to claim 28 wherein the apparatus modules have a combined weight of 15 pounds or less.

30. A method according to claim 22 wherein the apparatus provides a maximum pressure of about 60 mm Hg or less.

31. A method according to claim 22 wherein the rotating blade is used to establish and determine the rate and duration of air pulses entering the bladder.

32. A method according to claim 22 wherein the pulses include one or more minor perturbations or fluctuations within and/or between individual waves.

33. A method of making a chest compression apparatus, comprising the steps of providing or combining:
   a) a mechanism for applying a force to the thoracic region of a person, the mechanism comprising a bladder for receiving pressurized air, and
   b) a mechanism comprising a motor-driven rotating blade adapted to periodically interrupt the stream of pressurized air to the bladder, in order to provide pressure pulses having a substantially sinusoidal wave form that comprises a fast rise, sine wave when applied at a frequency of 6 Hz,
   c) and a mechanism for venting the pressurized air from the bladder.

34. A method according to claim 33 wherein the apparatus comprises a plurality of components, including an air flow generator component, a pulse frequency control component, a pressure control component, and a patient vest, wherein the pulse frequency control and pressure control components can, independently, be used by the patient or can be preset and determined by the manufacturer or physician so as to deliver compression pulses having substantially sinusoidal wave forms.

35. A method according to claim 34 wherein the pulse frequency control component is programmed and controlled electronically to allow for the automatic timed cycling of frequencies.

36. A method according to claim 33 wherein the apparatus comprises
   a) an air flow generator component adapted to provide a continuous stream of pressurized air,
   b) a pulse frequency control component in flowable communication with the air flow generator, and
   c) a patient vest adapted to be worn by a user in order to receive the pulses in the form of corresponding force applied to the thoracic region.

37. A method according to claim 36 wherein the apparatus further comprises a pressure control component in flowable communication with the pulse frequency control component and adapted to permit a user to control the pressure of the pulses.

38. A method according to claim 33 wherein the apparatus is provided in the form of a plurality of portable modules having a combined weight of about 20 pounds or less.

39. A method according to claim 38 wherein the apparatus provides a maximum pressure of about 60 mm Hg or less.

40. A method according to claim 33 wherein the pulses include one or more minor perturbations or fluctuations within and/or between individual waves.

* * * * *